US006386707B1

(12) United States Patent
Pellicano (10) Patent No.: US 6,386,707 B1
(45) Date of Patent: May 14, 2002

(54) METHOD FOR EVALUATING VISUAL ACUITY OVER THE INTERNET

(76) Inventor: Russell A. Pellicano, 9680 N. Bayview Rd., Southold, NY (US) 11971

( * ) Notice: Subject to any disclaimer, the term of this patent is extended or adjusted under 35 U.S.C. 154(b) by 0 days.

(21) Appl. No.: 09/435,048

(22) Filed: Nov. 8, 1999

(51) Int. Cl.⁷ .................................................. A61B 3/00
(52) U.S. Cl. ...................................................... 351/246
(58) Field of Search ................................ 351/201, 202, 351/203, 205, 209, 222, 224, 233, 237, 238, 246, 243, 223

(56) References Cited

U.S. PATENT DOCUMENTS

| | | | |
|---|---|---|---|
| 5,892,570 A | * 4/1999 | Stevens | ....................... 351/237 |
| 5,914,772 A | 6/1999 | Dyer | |
| 5,940,802 A | 8/1999 | Hildebrand et al. | |
| 5,953,102 A | 9/1999 | Berry | |
| 5,956,121 A | * 10/1999 | Hosoi et al. | ................. 351/205 |
| 6,033,076 A | * 3/2000 | Brauning et al. | ........... 351/224 |

* cited by examiner

Primary Examiner—George Manuel
(74) Attorney, Agent, or Firm—Scully, Scott, Murphy & Presser (57) ABSTRACT

The present invention is a method for evaluating visual acuity of a user, performed on a computer connected to a server via an Internet. After the evaluation starts, the user is asked to provide information including a name, a brief medical history and the eye prescription information. The evaluation of the user is performed by providing the reading, color determination, distance, dyslexia, peripheral vision, and depth perception tests. A treatment suggestion is produced indicating that no further action is necessary, medical intervention is necessary, or that a vision problem is detected and may be corrected by eyeglasses. The selection allows the user to select eyeglasses frames, order eyeglasses, and repeat the evaluation after the eyeglasses are received.

30 Claims, 11 Drawing Sheets

Pinhole Tests

Figure 9(c)

METHOD FOR EVALUATING VISUAL ACUITY OVER THE INTERNET

BACKGROUND OF THE INVENTION

1. Field of the Invention

The invention relates to systems for testing vision and dispensing eyeglasses, and more specifically to an interactive system and methodology for conducting vision examinations and prescribing eyeglasses over the Internet.

2. Description of Prior Art

The natural effects of aging and eyestrain induced by long exposure to television or computer monitors can each induce changes in vision that requires correction lenses for the human eye. In most cases, a visit to an ophthalmologist or optometrist for an eye exam generates a prescription for eyeglasses or contact lenses which is then filled by a specialty optical store that enables the customer to select the desired frames for their personal lenses.

Today, more and more products and services may be contracted and purchased through e-commerce transactions over the Internet. The Internet is able to bring scarce resources and locally unavailable services to disenfranchised and distant communities. On-line shopping saves time and money when the quality of goods to be purchased is known. Recent developments in e-commerce has enabled on-line shopping with consumer credit cards.

Currently, an optometrist or ophthalmologist analyzes the patient's vision and generates prescriptions in a scheduled appointment. The optometrist normally fits the patient with clinical test lenses to read an eye chart posted some distance away, and adjusts the lenses until the optometrist is satisfied. The patient does not normally expect a retest after the prescription is filled. In some instances, the eyeglasses may not fully correct a patient's vision and may even be harmful to the patient. Once the prescription is filled, the eyeglass shop will not redo the glasses because they followed the prescription provided by the optometrist. To change the prescription the patient must revisit the optometrist.

The present invention enables an eye test which may be taken in the comfort of the patient's own home, as many times as the patient feels necessary, without the hassle of making and keeping appointments, and without the anxiety associated with visits to a doctor's office. Furthermore, after the eyeglasses are made, the patient is able to retest the vision and, if necessary, return the glasses to be remade until fully satisfied.

SUMMARY OF THE INVENTION

The invention provides a comprehensive testing platform including an interactive Internet server for determining the visual acuity of a test subject. The test subject may use an inventive intelligent vision interface connected to the interaction server over the Internet. The vision testing provided by the invention may be varied in accordance with the prior test results of the subject, the subject's medical history, and information derived from a current eyeglass prescription. The vision test may include: a reading vision test, a distance vision test, a color determination test, a test for dyslexia, and peripheral vision and depth perception tests. The invention may also use age appropriate graphics and sounds, e.g., cat, dog, bus, car, etc., to test visual acuity in younger children.

To start the test, the test subject connects their PC to the inventive interactive server using any commercially available Internet Service Provider and browser. Following a successful logon, a help sheet is printed and/or displayed on the test subject' computer. The help sheet is then used to help establish the monitor size and resolution, which is determinative in the resolution of the text and graphic text figures. A measuring guide may also be provided to determine the size of glasses and the distance between the eyes of the subject. The instructions to guide the test subject through the test are available in printed form, audio playback, and automatic screen help queues.

To determine visual acuity, the test subject is instructed to remain a given distance from the screen and to focus attention on a specified graphic or text displayed on the test subject's computer screen. The test subject is then instructed to respond to the text and audio instructions via a computer mouse, a keyboard or audio command selections. To determine the test subject's visual acuity, input from the subject's responses to questions is used to vary the text content in size, clarity, spacing and contrast until the test subject determines that the text is recognizable at the given distance. The basic color testing may include a number of letters embedded in a figure in hues of selected colors and graininess. Adults may be asked to supervise children in the reading and color testing.

The vision test also incorporates a number of two and three-dimensional images containing visual triggers that must be responded to by the test subject, such as reading a three-dimensional character presented as a distant figure, e.g., a stop sign, in a three-dimensional street scene for example. The peripheral vision test may be included with this test sequence.

BRIEF DESCRIPTION OF DRAWINGS

The foregoing objects and advantages of the present invention may be more readily understood by one skilled in the art with reference being had to the following detailed description of a preferred embodiment thereof, taken in conjunction with the accompanying drawings wherein like elements are designated by identical reference numerals throughout the several views, and in which.

DETAILED DESCRIPTION OF THE INVENTION

Figure 1A:
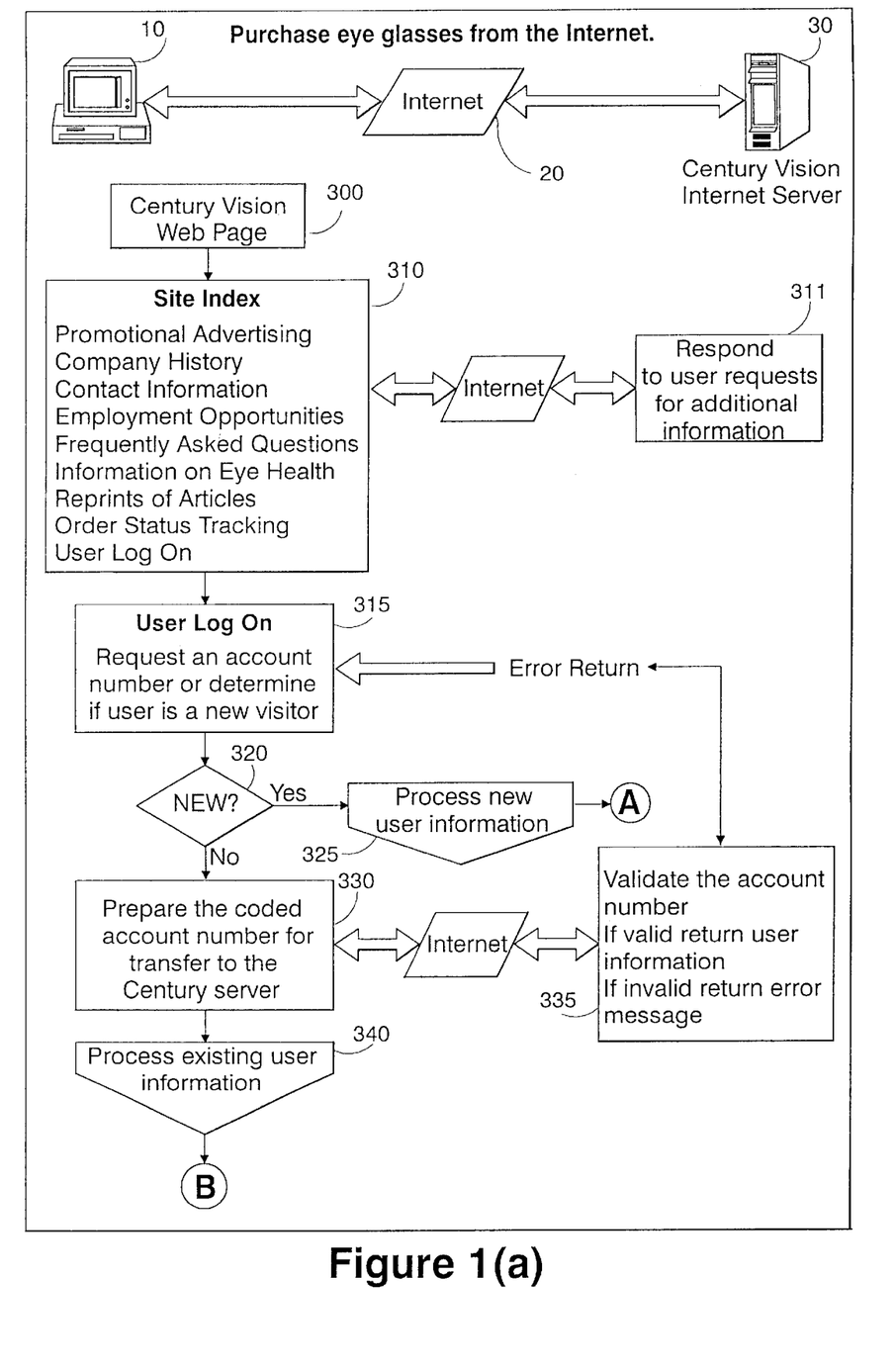
FIGS. 1(a) and 1(b) are flowcharts depicting the interaction via the Internet of the test subject's computer and the Century Visions server (CVS) of the invention.

As shown in FIG. 1(a) (1), a browser is used to connect a test subject's computer terminal 10 to a Century Vision Internet server (CVS) 30 via the Internet 20. It is understood that any commercially available internet browser, such as Microsoft Internet Explorer® or Netscape Navigator®, may be used.

As shown at FIG. 1(a) (2), once a connection is made with the CVS server 30, a Century vision web page is downloaded to the test subject's terminal 10 for display as indicated at step 300. Then, at step 310, a site index is displayed which may incorporate information, including, but not limited to, a user logon entry field, promotional advertising, company history, contact information, employment opportunities, frequently asked questions, information on eye health, reprints of articles, order status tracking, and more. Additionally, at step 310, the test subject may request additional information. The Century vision Internet server 30 responds to the request, at step 311, and supplies additional information via the Internet 20.

If the test subject requested the user logon entry from the site index, then at step 315 the test subject's account number and an optional password is requested. After such account/password information is supplied, a determination is made at step 320 as to whether the logon is being attempted by a new or an existing user. If the test subject is determined to be a new user the processing continues at step 325. If however, the test subject is determined to be a pre-existing user, step 330 prepares a coded account number for transfer to the Century vision Internet server 30 via the Internet 20 for the validation of the account number. At step 335, if the account number is valid, the test subject information is retrieved and displayed on the test subject computer terminal 10 and the existing test subject processing continues at step 340. If the account number is invalid, an error message is sent from the Century vision Internet server 30 to the test subject terminal 10 where the user is prompted for new logon input at step 315.

Figure 1B:
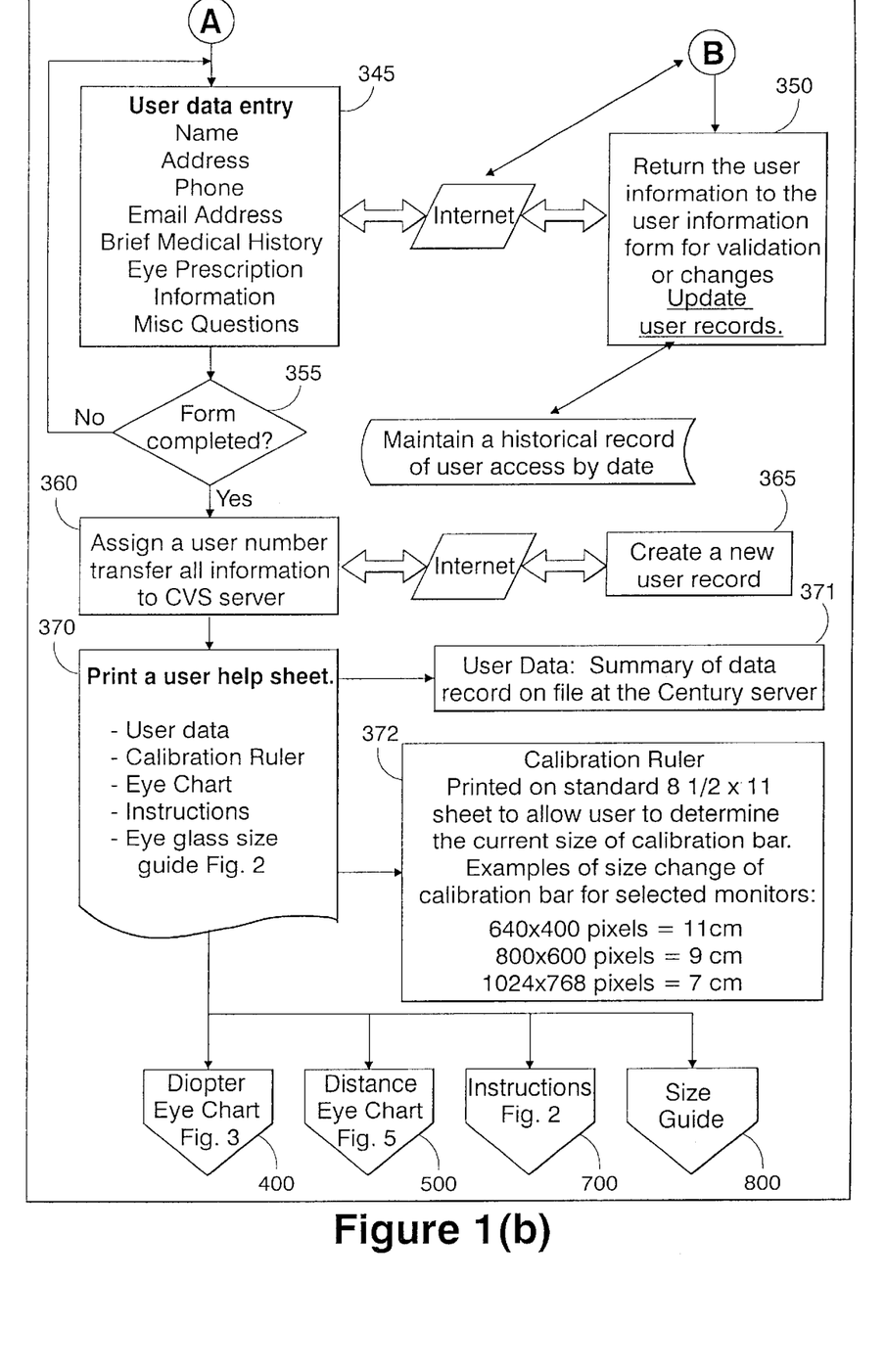

As illustrated in FIG. 1(b), at step 345, a new test subject is asked to fill out a blank questionnaire which may request information such as: the test subject's name, address, phone number, e-mail address, brief medical history, eye prescription information and other dynamic miscellaneous questions. Alternately, an existing test subject is asked to verify a questionnaire filled in with previously supplied information retrieved at step 335.

Upon indication that all mandatory questions are answered, a determination is made at step 355 as to whether the questionnaire form is incomplete, in which case step 345 is repeated. When it is determined that the test subject questionnaire is complete, the user's record and the historical record of access are updated at step 350. At step 360, a test subject number is assigned to the new test subject, and all entered information is transferred to the Century Vision Server (CVS) 30, which creates a new user record at step 365.

Figure 2:
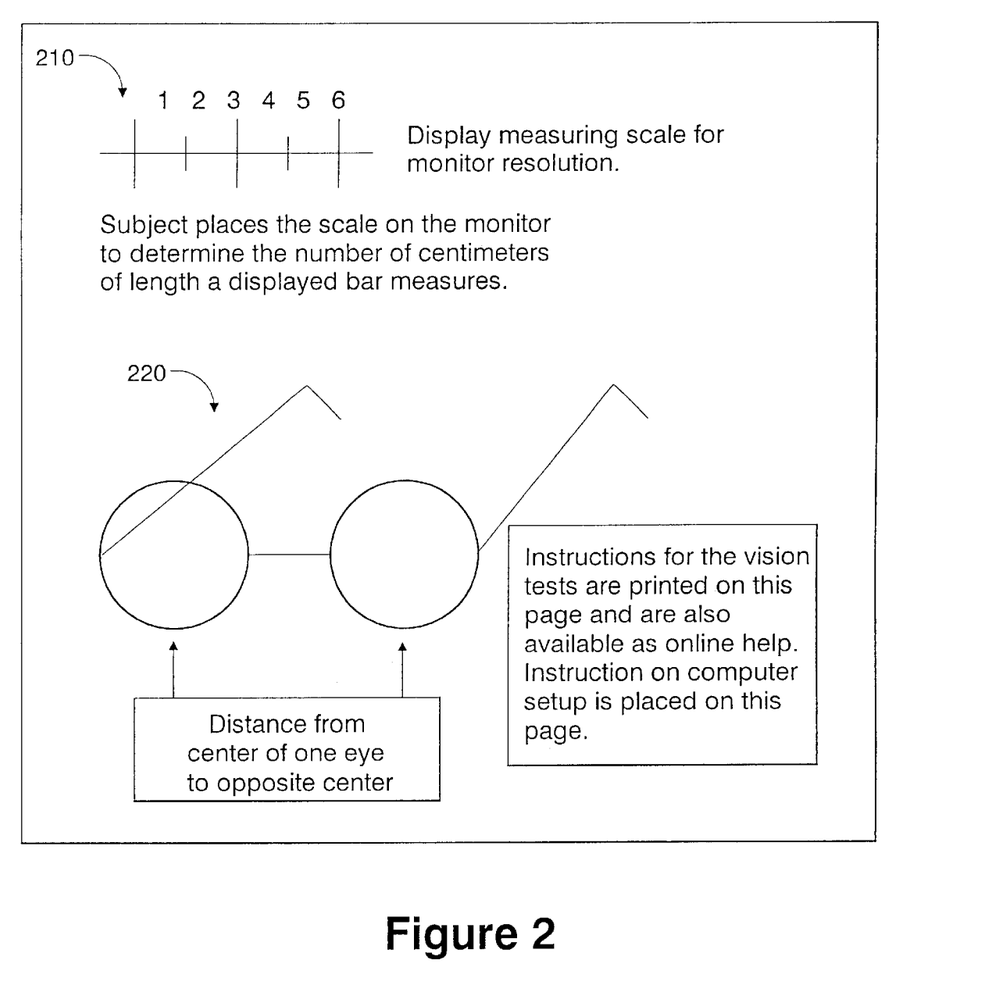
FIG. 2 is a measuring guide for determining the size of glasses and the distance between eyes.

At step 370, a help sheet is printed on a printer attached to the test subject computer. As shown in FIG. 2, the help sheet may contain the measuring scale 210 used to help establish the monitor resolution, determinative of the resolution of the text and graphic text figures. Furthermore, the eye glass size measuring guide 220 is provided to determine the size of glasses and the distance between eyes. The instructions to guide the test subject through the test are available in printed form, audio playback, and automatic screen help queues.

Returning briefly to FIG. 1(b), the help sheet may also include: a summary of the data on file 371 at the Century vision Internet server 30; a calibration ruler 372, e.g., printed on a standard 8½×11 sheet to allow test subject to determine the current size of calibration bar; an eye chart; and, instructions. At this point the system is ready to conduct the vision acuity test.

Figure 3:
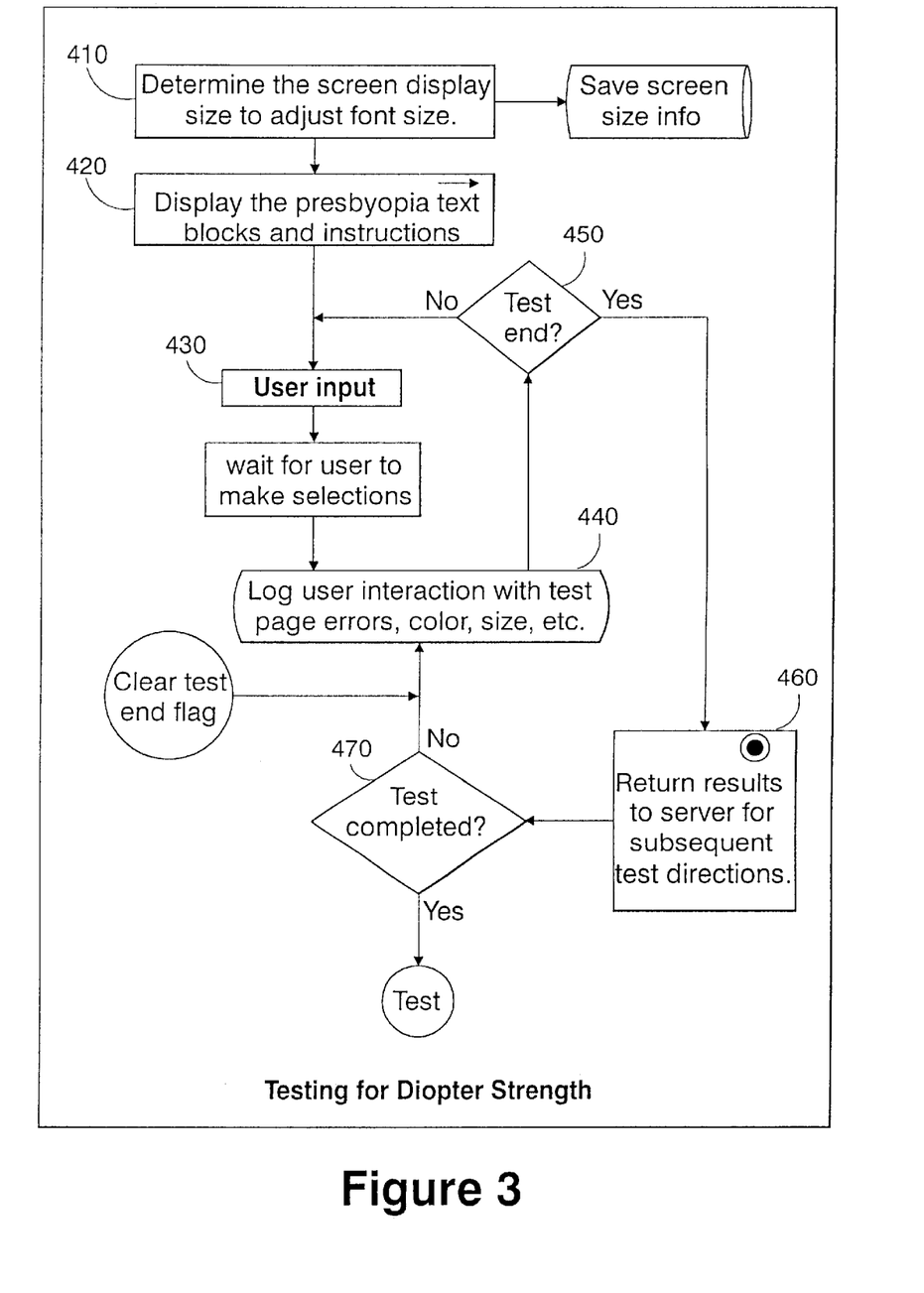
FIG. 3 is a flow diagram of steps in executing a diopter strength test.

The present invention incorporates a variety of vision acuity tests including: a diopter strength test 400; a distance vision test 500; tests for visual distortion, astigmatism and dyslexia; and tests for emmetropia, myopia and hypermetropia. As shown in FIG. 3, at step 410, a determination of the screen display size of the test subject's computer terminal is made so that the text/character font size displayed may be adjusted. Additionally, at step 415, the screen size information is saved in a file. Then, at step 420, a presbyopia text block and related instructions as shown in FIG. 4, are displayed or printed.

Figure 4:
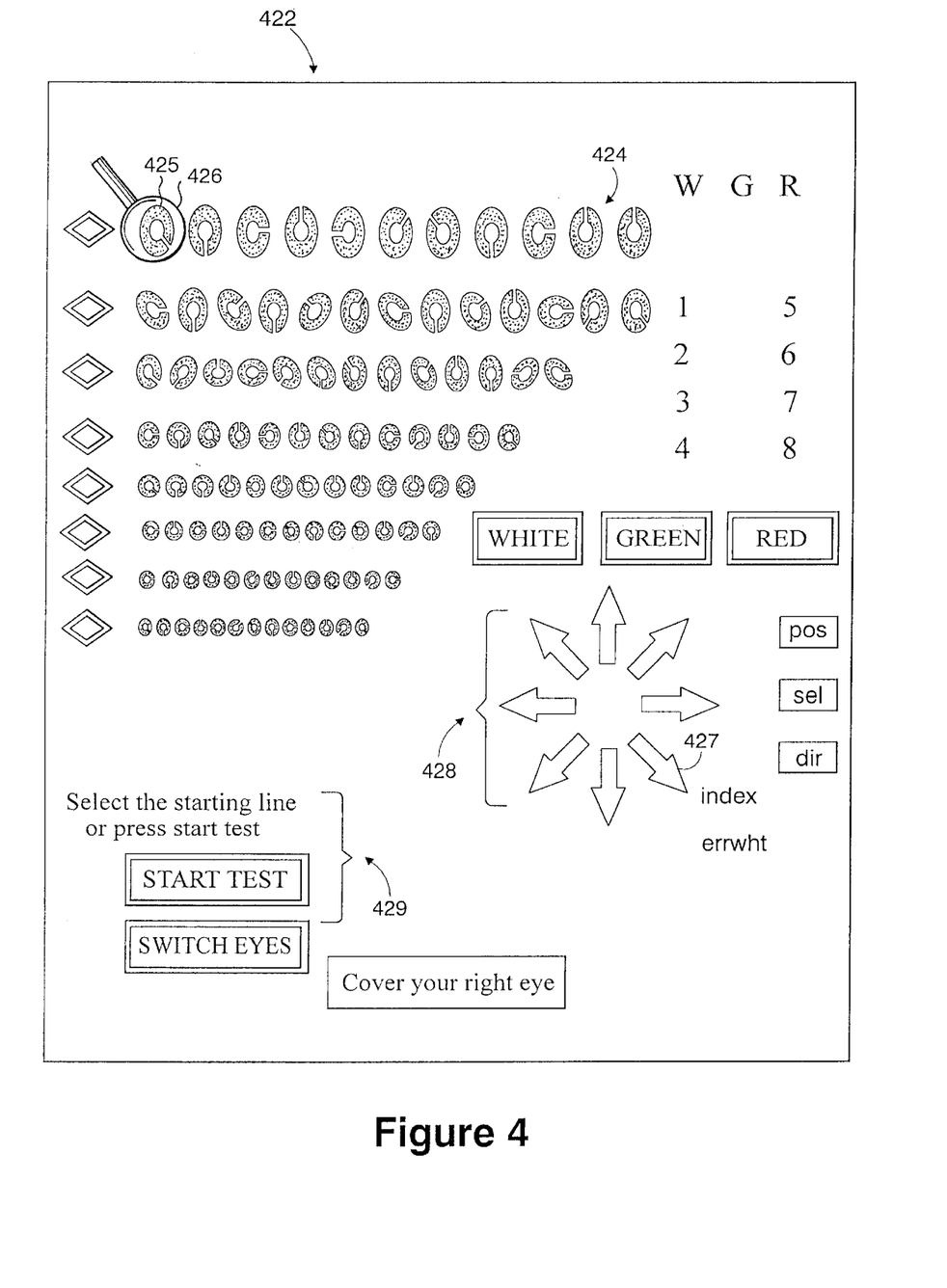
FIG. 4 is an example Internet test page used by the subject to interact with the Century Vision Server.

Particularly, FIG. 4 illustrates a test page 422 displayed to the user for testing a subject for presbyopia. This test requires the subject to select the direction arrow 428 corresponding to the orientation of the character "C" in a test block line 424 that is highlighted by a displayed magnifying glass 426. For example, the first character "C" 425 shown highlighted in FIG. 4, is oriented at 315° degrees. The proper selection would be the arrow at the same orientation, e.g., the arrow 427. The subject may select any line 424 to start the test or begin at the first line. Repeated errors in one of the eight orientations shown provide insight into the possibility of astigmatism for each eye. The final astigmatism grid, as described herein in view of FIG. 7(b), will confirm the indications shown in the test supported by the test of FIG. 4. In addition, according to this test methodology, if more than two errors occur, the line is repeated with first a green background and then a red. This color change provides a refinement of visual acuity which accounts for a change in diopter strength, plus or minus, in the subject's focus point. As shown by the instructions 429 provided in the test page of FIG. 4, the test subject is instructed to read each line with each eye individually, and then with both eyes.

Returning to FIG. 3, the system waits for test subject interactions at step 430, which input may be provided via a computer mouse, a keyboard or audio means. After receiving test subject interactions for this test (FIG. 4), e.g., errors, colors and selected sizes, etc., the inputs are logged in the CVS server at step 440. A determination to end the test is then made at step 450 based on the test subject input and whether any further screen display adjustments may be made. If, at step 450, the decision is to continue with the test, then the system waits for further test subject input at step 430. If, however the decision is to end the test, the test results are uploaded to the Century vision Internet server 30 [FIG. 1(a)] for subsequent test directions. If the Century vision Internet server 30 determines at step 470 that the test is not completed, control is passed to step 440 to log further user test interaction. Otherwise, the system may conduct a color vision test which directs the test subject to read a number of letters embedded in a figure of selected hues, colors and graininess (not shown). Adults may be asked to supervise children in the reading and color testing.

Figure 5:
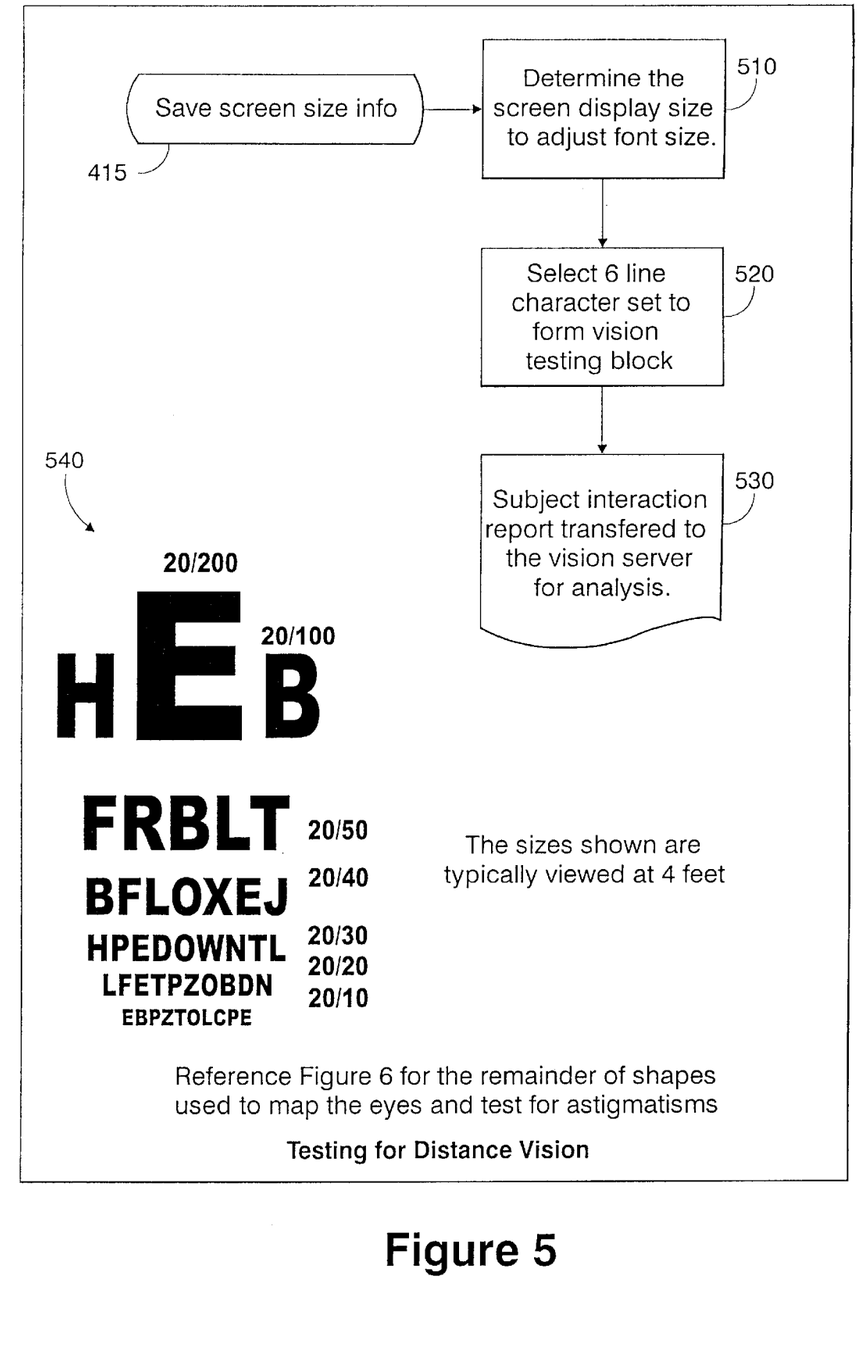
FIG. 5 is an example of an eye chart and a flow of steps used for distance vision testing.

The distance vision test is now described herein with respect to in FIG. 5. It is understood that the interactive test page depicted in FIG. 4 may be used in conjunction or as a replacement to FIG. 5 with the size and spacing of the characters being different from the distance shown in FIG. 4. As shown in FIG. 5 at step 510, the screen display size information previously saved at the beginning of the first test, is now loaded from the file 415 so that displayed character fonts may be adjusted. The distance vision test may be given for each eye individually and then for both eyes together. At step 520, the test subject is instructed to select a six-line character set 540 forming a vision testing block. Each time the distance test is initiated, a different character sequence may be generated for the six line character set 540. At step 530, the test subject selections are accepted and a corresponding subject interaction report is generated and uploaded to the Century vision Internet server 30 [FIG. 1(*a*)] for analysis.

Figure 6:
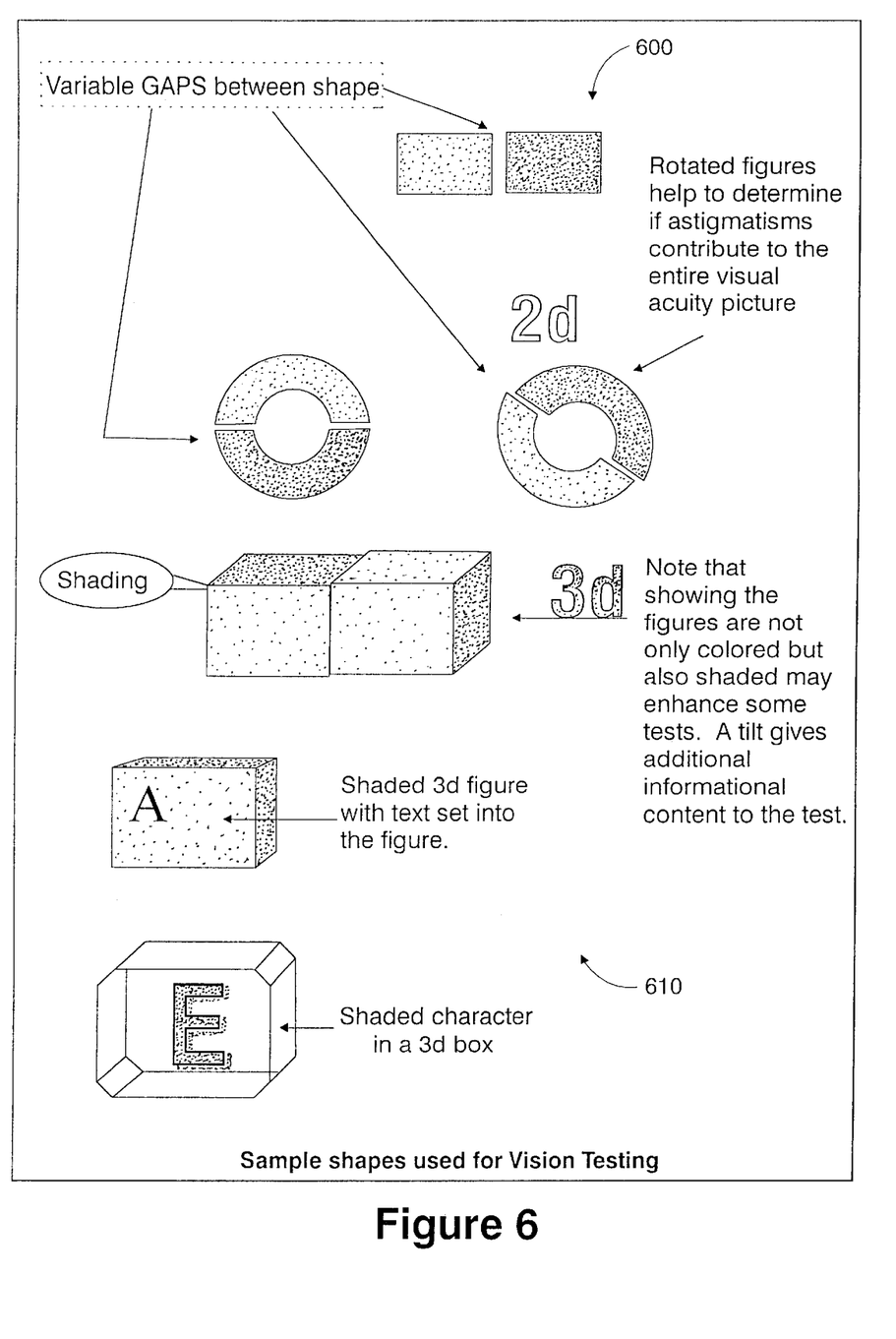
FIG. 6 is an example of shapes used for distance vision testing.

The common distance vision test using the alphabetic set of sized characters 540 may be followed by one or more tests for determining astigmatism, such as shown in FIG. 6. These tests require the display of two-dimensional and three-dimensional objects such as spheres, cubes, trapezoids, etc., that may be proportionally divided. For example, some divisions may be 50% while others are divided into other proportions. The divisions may be determined by the test criterion and may be modified by the Century vision Internet server 30 [FIG. 1(*a*)] during the course of the test. The Century vision Internet server 30 evaluates the interim results and after determining adjustments to the next series of tests, downloads new adjusted test tables for the next series.

The first series of tests may be performed using only the objects against a flat background 600. The sizes, gap separation, tilt angles, color, shading and illuminations of the displayed objects are variables determined by the initial questionnaire and interim test results from a summation of completed tests. In this series of tests, the object shape size may be varied by at least 12 steps, for example, gap separation may vary by no less than 8 steps, for example, and object colors are selected to determine if color sensitivity exists for each shape utilized. Furthermore, color illuminations and contrasts are used to determine vision sensitivity to lighting conditions.

The second series of tests requires the presentation of the three-dimensional objects 610 into a three-dimensional scene. This enables the test subject's eyes (and brain) to relax so that the eye does not accommodate the vision correction for near/far distance acuity. A similar series of tests may be performed to determine whether the test subject is able to discern visible separations of the three-dimensional objects. As with the first series of tests, the size, gap separation, color and illumination are adjusted to compare the results of both series.

Figure 7A:
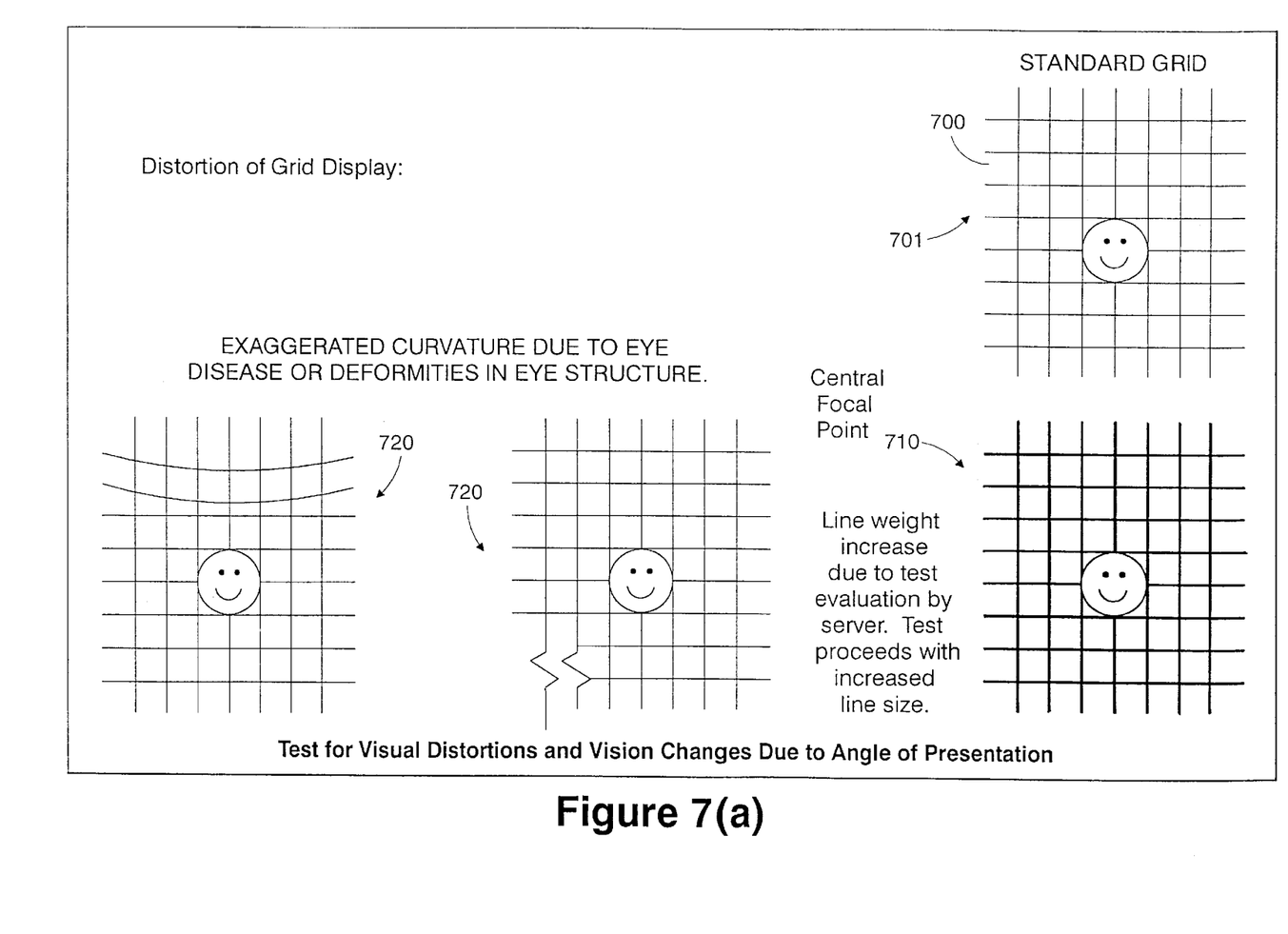
FIG. 7(a) is an example of the test for visual distortions and vision changes due to an angle of presentation.

A test for visual distortions and vision changes due to an angle of object presentation may be further conducted, as shown in FIG. 7(*a*). These tests enable the determination of whether the test subject has a problem in seeing a complete grid of lines 700. Distortions are denoted by the interaction of the subject selecting the extends of the distortion in the grid 700. The test subject places the mouse curser on the center of the distortion and then at the furthest point in the distortion area. A central focal point 701 is provided at the center of grid 700. The subject is then directed to maintain the eye focus at the center point when determining if distortions appear. The test subject views a starting grid size of 20×20 single point lines and progresses to a test of 120×120 lines. Additional grid lines may be added by the vision server during this test sequence. The grid line weight or thickness 710 may be increased according to the test subject's interactions. Furthermore, to determine if the curvature makes the grid lines appear straighter to test subjects with eye disease or deformities in the eye structure, the grid line curvature may be exaggerated 720 to adjust the distortion in reverse.

Figure 7B:
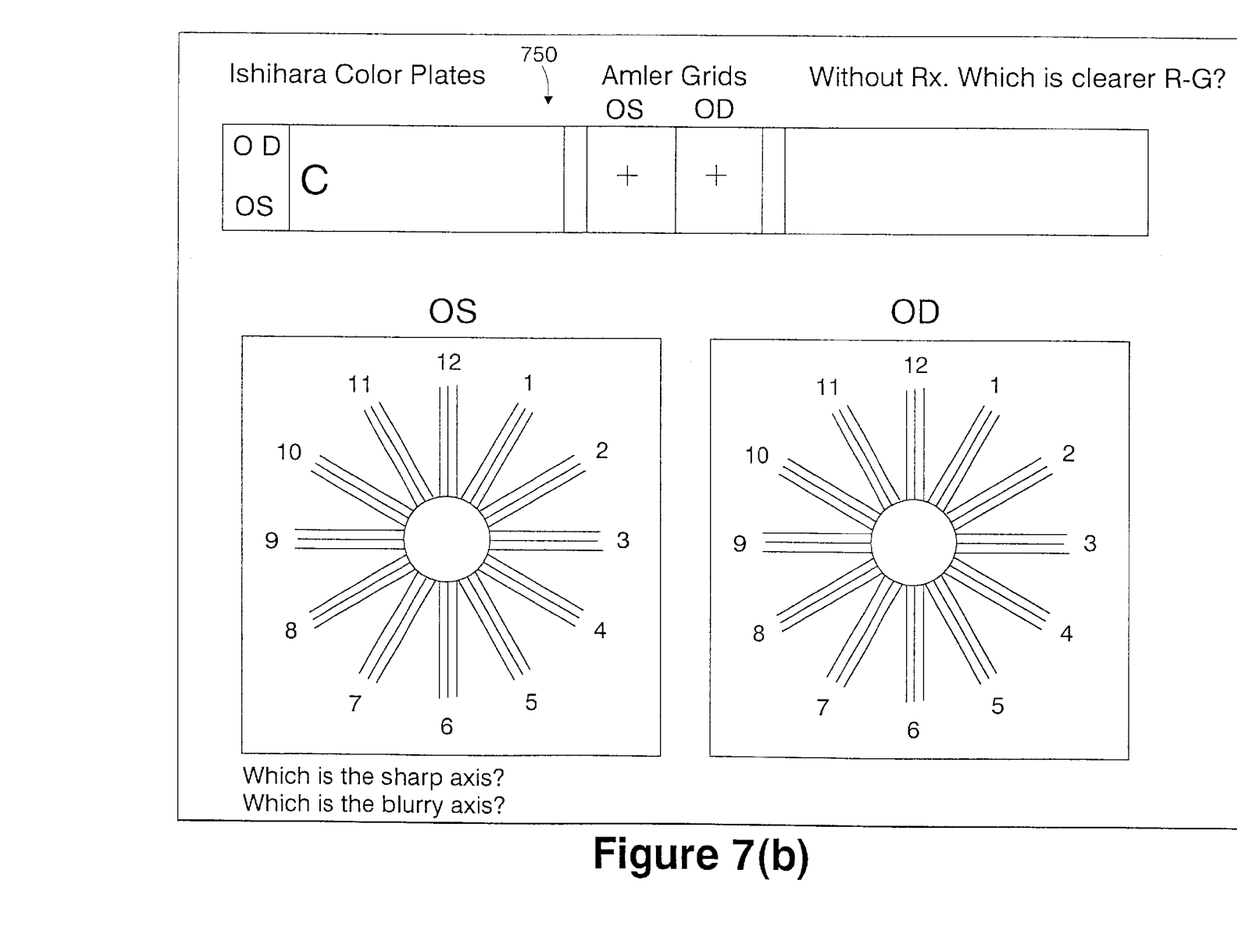
FIG. 7(b) is an example of another visual acuity test for astigmatism.

FIG. 7(*b*) is an illustration depicting the presentation/display of Amler grids 750 to enable the determination of whether the test subject's vision needs to be corrected for astigmatism. This astigmatism grid may be presented in the form depicted in FIG. 7(*b*) or, may be dynamically presented, e.g., in animated form. For example, the test subject will be prompted to enter which presented display has the sharper axis, which entry may be used in the evaluation of whether the test subject's vision exhibits need for astigmatic correction.

Figure 8:
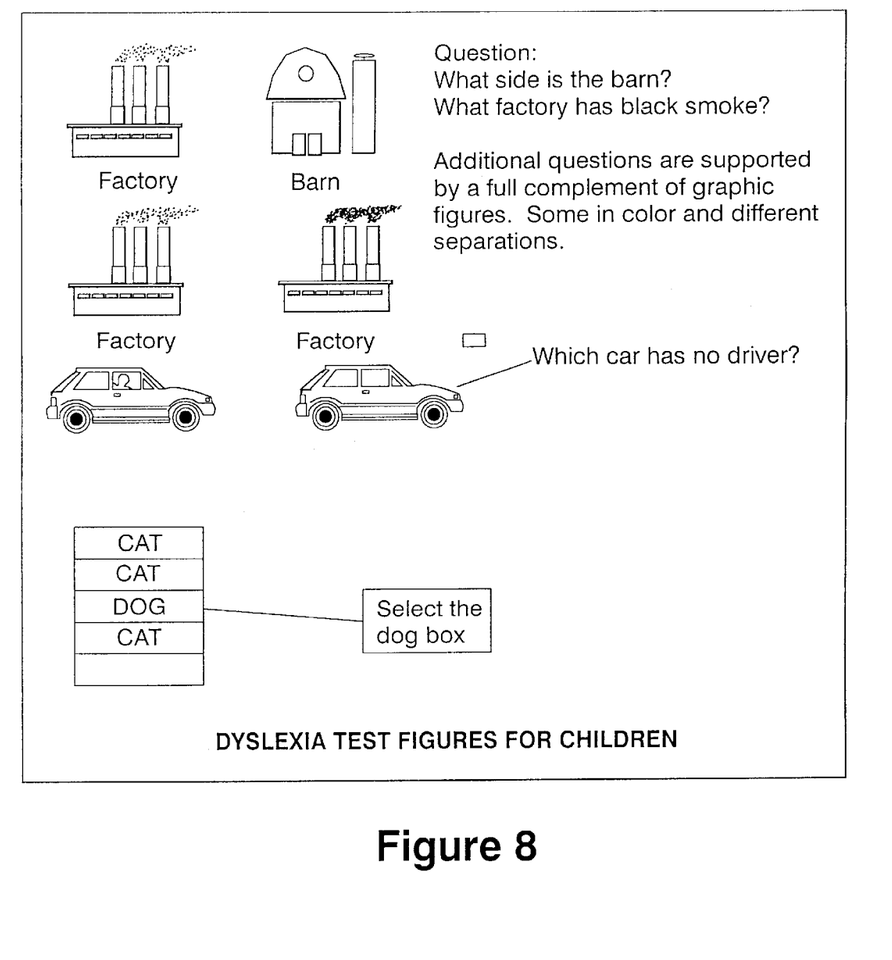
FIG. 8 is the interactive chart for the test for dyslexia.

The invention may also provide a visual test for dyslexia. As shown in FIG. 8, the chart text may be adjusted to accommodate test subjects ranging from the young children to adults, using information obtained in prior tests. The dyslexia test is for screening only and if the test subject is a minor must be supervised by an adult. In the example screen display as shown in FIG. 8, the test will be accompanied by questions requiring the subject to identify an object e.g., the barn, the factory spewing black smoke, or which car has the driver.

Figure 9A:
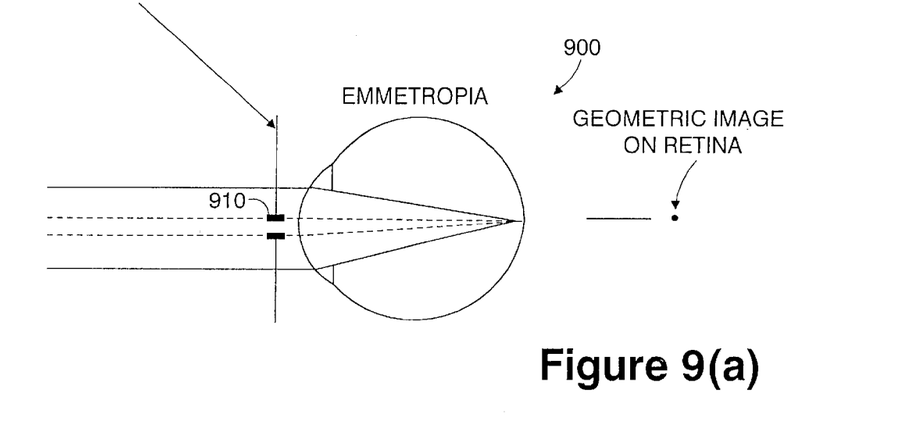
FIGS. 9(a)–9(c) illustrate the pin hole test used to test for emmetropia, myopia or hypermetropia.
Figure 9B:
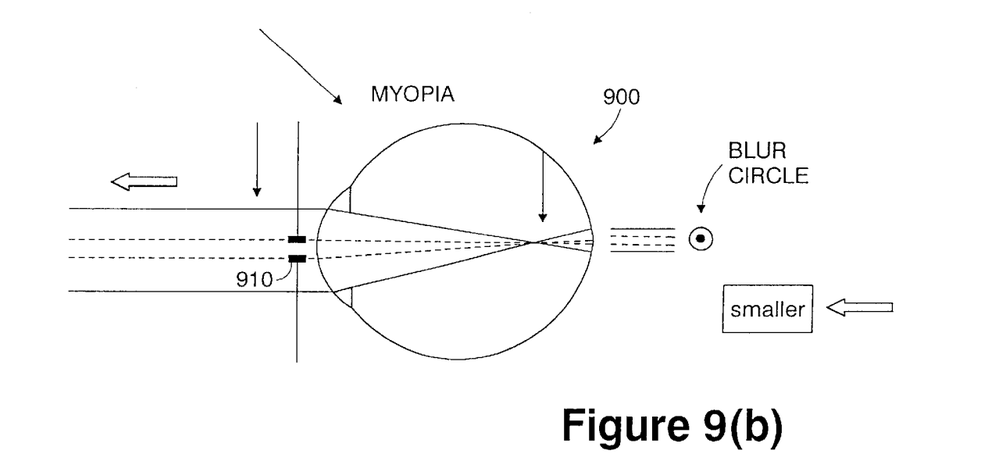
Figure 9C:
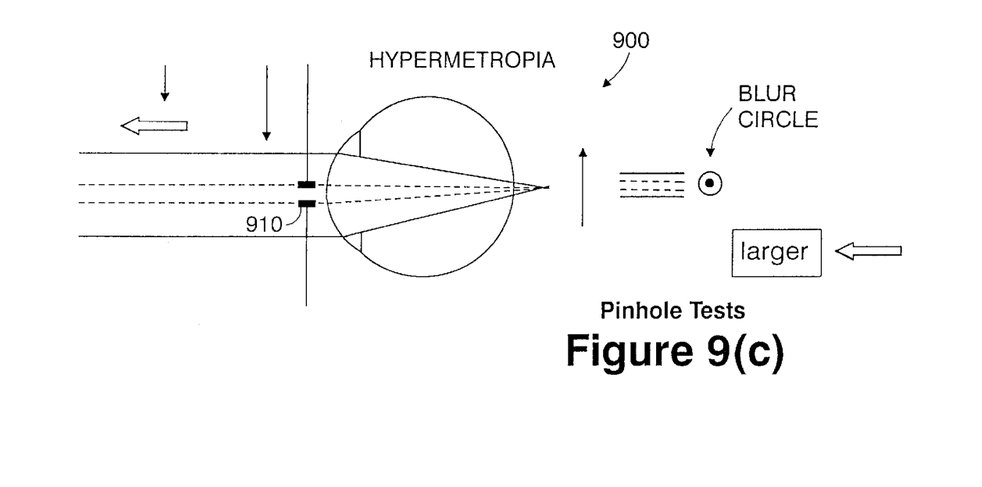

The invention may also provide a "pin hole" test 900 used for determining whether a test subject exhibits emmetropia, myopia or hypermetropia conditions. According to this test, as shown in FIGS. 9(*a*)–9(*c*), the subject is instructed to use the pinhole 910 provided to observe a target on the computer display screen and determine whether the object becomes larger or smaller with corresponding in/out movement of the pin hole. On moving the pin hole away from the eye, if the error is uncorrected myopia, the target will get smaller. A subject exhibiting hypermetropia will determine that the target has expanded. As a second verification, side to side movement of the pin hole is effected to determine if the direction of the target is with the movement, indicating myopia, or against the target, indicating hypermetropia. It is understood that both conditions will cause a blurred far vision in the subject. The instructions for this test will be provided on the help sheet instructions.

In all the visual acuity tests described herein, a random sequence generator is implemented for the generating character, audio and three-dimensional scenes. All of the test results are transferred to the Century vision Internet server 30 [FIG. 1(*a*)] for evaluation by an expert system that diagnoses and recommends prescription or further tests. When all tests are exhausted and the client has entered all the requested information into the computer, the Century vision Internet server 30 makes an evaluation of the results and suggests appropriate action. If the server determines that the client's vision is normal, the client is advised that no vision correction is necessary at this time and that after an appropriate period the vision test should be re-taken. The client may then be offered other eye care products such as sunglasses, safety and PC glasses. If a determination is made that medical involvement is necessary, the client will be advised of that fact and a list of local eye doctors may be displayed or printed.

Otherwise, the client may be asked to select eyeglass frames from a displayed list of frames, and additionally may zoom in for closer examination of a particular frame. After the frame is selected, the client may choose a method of payment, and continue to browse the web site for other eye care products such as sunglasses.

After the purchased eyeglasses are delivered to the client, the client is requested to retake the eye test to verify that the original evaluation was correct and properly executed. An e-mail prompt may be sent to the client until the test is re-taken and the evaluation is confirmed.

The interactive system of the invention may be extremely well suited to test the vision of users wearing LCD screen glasses which may function as monitors instead of conventional television a computer screens. Additionally, the invention is well suited for testing vision of users of virtual reality helmets. As it is impossible to wear regular glasses under the LCD screen glasses or the virtual reality helmets, the invention may thus be used to adjust, or distort the individual screen views according to the subjects' vision pattern to allow subjects with bad vision to use those devices without the use of eyeglasses or contact lenses.

Furthermore, the invention may be executed on a computer without the use of the Internet by moving all the functionality of the server to the test subject's computer. In this case, a diskette with test results may be sent out for evaluation, or having evaluated information locally, a purchase of glasses request may be mailed, or e-mailed.

While the invention has been particularly shown and described with respect to illustrative and preferred embodiments thereof, it will be understood by those skilled in the art that the foregoing and other changes in form and details may be made therein without departing from the spirit and scope of the invention that should be limited only by the scope of the appended claims.

What is claimed is:

1. An interactive method for evaluating visual acuity of a user, said evaluation performed on a terminal of a computer connected to a server via a network, said server enabling visual acuity tests to be performed by said user unaided, the method comprising the steps of:
   a. said server modulating a test display size for said terminal according to terminal measurements supplied by said user;
   b. displaying a first vision test on said terminal according to said terminal measurements and user supplied information;
   c. accepting and communicating user replies to said first vision test to said server via a computer graphical interface;
   d. displaying a subsequent vision test generated by said server according to said terminal measurements and to said user replies;
   e. accepting and communicating user replies to said subsequent vision test to said server via said computer graphical interface;
   f. repeating steps d) and e) until all vision tests appropriate for said user are performed, said vision tests including one or more tests selected from the group comprising: a reading test, a color determination test, a distance vision test, a dyslexia test, a peripheral vision test, and a depth perception vision test; and
   g. said server producing a treatment suggestion by analyzing results of said performed evaluation.

2. The method of claim 1, wherein said computer graphical interface is a common Internet browser.

3. The method of claim 1, further comprising the step of displaying and printing a help sheet to enable said user to determine said terminal measurements.

4. The method of claim 3, wherein said help sheet comprises a calibration ruler to determine screen resolution of said terminal.

5. The method of claim 1, wherein said user supplied information comprises a name and a brief medical history including eye prescription information.

6. The method of claim 5, wherein said user supplied information is stored and is automatically retrieved every time said evaluation is performed for said user.

7. The method of claim 1, wherein said treatment suggestion comprises the following indications:
   a vision problem was not detected and no further action is necessary;
   a vision problem was detected and medical intervention is necessary; and
   a vision problem was detected and may be corrected by eyeglasses.

8. The method of claim 7, wherein if medical intervention is necessary, the step of offering a referral to medical professionals.

9. The method of claim 8, further comprising steps of:
   selecting eyeglasses frames from a presented list;
   requesting eyeglasses to be manufactured according to said treatment suggestion;
   receiving said eyeglasses; and
   repeating said evaluation of visual acuity of said user while wearing said received eyeglasses.

10. An interactive method for evaluating visual acuity of a user, said evaluation performed on a terminal of a computer for enabling visual acuity tests to be performed by said user unaided, the method comprising the steps of:
    a. displaying and printing a help sheet including a calibration ruler for determining screen resolution and enabling said user to determine terminal measurements;
    b. modulating a test display size for said terminal according to terminal measurements supplied by said user;
    c. displaying a first vision test on said terminal according to said terminal measurements and user supplied information;
    d. accepting user replies to said first vision test;
    e. displaying a subsequent vision test generated by said server according to said terminal measurements and to said user replies;
    f. accepting user replies to said subsequent vision test;
    g. repeating steps e) and f) until all vision tests appropriate for said user are performed, said vision tests including one or more tests selected from the group comprising: a reading test, a color determination test, a distance vision test, a dyslexia test, a peripheral vision test, and a depth perception vision test; and
    h. producing a treatment suggestion by analyzing results of said performed evaluation on said computer.

11. The method of claim 10, wherein said user supplied information comprises a name and a brief medical history including eye prescription information, the method including storing said supplied information after a first evaluation and automatically retrieving said supplied information every time said evaluation is performed for said user.

12. The method of claim 10, wherein said treatment suggestion comprises the following indications:
    a vision problem was not detected and no further action is necessary;
    a vision problem was detected and medical intervention is necessary; and
    a vision problem was detected and may be corrected by eyeglasses.

13. The method of claim 12, wherein if medical intervention, the step offering a referral to medical professionals.

14. The method of claim 13, further comprising steps of:
    selecting eyeglasses frames from a presented list;
    requesting eyeglasses to be manufactured according to said treatment suggestion;
    receiving said eyeglasses; and
    repeating said evaluation of visual acuity of said user while wearing said received eyeglasses.

15. The method of claim 14, wherein said requesting step is performed via an Internet e-mail and mail service.

16. A computer program device readable by a machine, tangibly embodying a program of instructions executable by a machine to perform method steps for evaluating visual acuity of a user, said evaluation performed on a terminal of a computer connected to a server via a network, the server enabling interactive visual acuity tests to be performed by said user unaided, the method comprising the steps of:

a. said server modulating a test display size for said terminal according to terminal measurements supplied by said user;

b. displaying a first vision test on said terminal according to said terminal measurements and user supplied information;

c. accepting and communicating user replies to said first vision test to said server via a computer graphical interface;

d. displaying a subsequent vision test generated by said server according to said terminal measurements and to said user replies;

e. accepting and communicating user replies to said subsequent vision test to said server via said computer graphical interface;

f. repeating steps d) and e) until all vision tests appropriate for said user are performed, said vision tests including one or more tests selected from the group comprising: a reading test, a color determination test, a distance vision test, a dyslexia test, a peripheral vision test, and a depth perception vision test; and g. said server producing a treatment suggestion by analyzing results of said performed evaluation.

17. The computer program device of claim 16, wherein said computer graphical interface is a common Internet browser.

18. The computer program device of claim 16, further comprising the step of displaying and printing a help sheet to enable said user to determine said terminal measurements.

19. The computer program device of claim 18, wherein said help sheet comprises a calibration ruler to determine screen resolution of said terminal.

20. The computer program device of claim 16, wherein said user supplied information comprises a name and a brief medical history including eye prescription information.

21. The computer program device of claim 20, wherein said user supplied information is stored and is automatically retrieved every time said evaluation is performed for said user.

22. The computer program device of claim 16, wherein said treatment suggestion comprises the following indications:

a vision problem was not detected and no further action is necessary;

a vision problem was detected and medical intervention is necessary; and a vision problem was detected and may be corrected by eyeglasses.

23. The computer program device of claim 22, wherein if medical intervention is necessary a referral to medical professionals is offered.

24. The computer program device of claim 23, further comprising steps of:

selecting eyeglasses frames from a presented list;

requesting eyeglasses to be manufactured according to said treatment suggestion;

receiving said eyeglasses; and repeating said evaluation of visual acuity of said user while wearing said received eyeglasses.

25. A computer program device readable by a machine, tangibly embodying a program of instructions executable by a machine to perform method steps for evaluating visual acuity of a user, said evaluation performed on a terminal of a computer for enabling interactive visual acuity tests to be performed by said user unaided, the method comprising the steps of:

a. displaying and printing a help sheet comprises a calibration ruler for determining screen resolution to enable said user to determine terminal measurements;

b. modulating a test display size for said terminal according to terminal measurements supplied by said user;

c. displaying a first vision test on said terminal according to said terminal measurements and user supplied information;

d. accepting user replies to said first vision test;

e. displaying a subsequent vision test generated by said server according to said terminal measurements and to said user replies;

f. accepting user replies to said subsequent vision test;

g. repeating steps e) and f) until all vision tests appropriate for said user are performed, said vision tests including one or more tests selected from the group comprising: a reading test, a color determination test, a distance vision test, a dyslexia test, a peripheral vision test, and a depth perception vision test; and h. producing a treatment suggestion by analyzing results of said performed evaluation on said computer.

26. The computer program device of claim 25, wherein said user supplied information comprising a name and a brief medical history including eye prescription information, is stored after a first evaluation and is automatically retrieved every time said evaluation is performed for said user.

27. The computer program device of claim 25, wherein said treatment suggestion comprises the following indications:

a vision problem was not detected and no further action is necessary;

a vision problem was detected and medical intervention is necessary; and a vision problem was detected and may be corrected by eyeglasses.

28. The computer program device of claim 27, wherein if medical intervention is necessary a referral to medical professionals is offered.

29. The computer program device of claim 28, further comprising steps of:

selecting eyeglasses frames from a presented list;

requesting eyeglasses to be manufactured according to said treatment suggestion;

receiving said eyeglasses; and repeating said evaluation of visual acuity of said user while wearing said received eyeglasses.

30. The computer program device of claim 29, wherein said requesting step is performed via an Internet e-mail and mail service.

* * * * *